(12) United States Patent
Vic et al.

(10) Patent No.: US 7,582,286 B2
(45) Date of Patent: Sep. 1, 2009

(54) PHOTOACTIVATABLE DIAZIRINE-ACTIVE AGENT COMPOUNDS, COMPOSITIONS COMPRISING THEM AND USES THEREOF

(75) Inventors: Gabin Vic, Venette (FR); Aude Livoreil, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/798,288

(22) Filed: May 11, 2007

(65) Prior Publication Data

US 2007/0212318 A1 Sep. 13, 2007

Related U.S. Application Data

(62) Division of application No. 10/436,050, filed on May 13, 2003, now Pat. No. 7,285,285.

(60) Provisional application No. 60/386,571, filed on Jun. 7, 2002.

(30) Foreign Application Priority Data

May 13, 2002 (FR) .................................. 02 05863

(51) Int. Cl.
*A61K 8/49* (2006.01)
*A61K 8/18* (2006.01)
*A61Q 5/00* (2006.01)
*A61Q 5/10* (2006.01)

(52) U.S. Cl. .................... 424/70.1; 424/70.2; 424/70.9; 424/70.11; 548/955; 548/957

(58) Field of Classification Search .................. 424/410, 424/70.1, 70.2, 70.9, 70.11; 548/955, 960, 548/957

See application file for complete search history.

(56) References Cited

U.S. PATENT DOCUMENTS

| 2,463,264 | A | 3/1949 | Graenacher et al. |
|---|---|---|---|
| 3,509,131 | A | 4/1970 | Church et al. |
| 3,525,736 | A | 8/1970 | Church et al. |
| 4,695,285 | A | 9/1987 | Chung-Bong-Chan et al. |
| 5,166,355 | A | 11/1992 | Leistner et al. |
| 5,237,071 | A | 8/1993 | Leistner et al. |
| 5,300,285 | A | 4/1994 | Halloran et al. |
| 5,585,091 | A | 12/1996 | Pelzer et al. |
| 5,994,341 | A * | 11/1999 | Hunter et al. ............... 514/449 |
| 6,159,455 | A | 12/2000 | Habeck et al. |
| 6,238,649 | B1 | 5/2001 | Habeck et al. |
| 2002/0022013 | A1 | 2/2002 | Leukel et al. |
| 2003/0113279 | A1 | 6/2003 | Vic et al. |

FOREIGN PATENT DOCUMENTS

| DE | 44 36 173 | 9/1996 |
|---|---|---|
| DE | 197 26 184 | 12/1998 |
| DE | 197 55 649 | 6/1999 |
| DE | 198 55 649 | 6/2000 |
| EP | 0 669 323 | 8/1995 |
| EP | 0 893 119 | 1/1999 |
| EP | 0 967 200 | 12/1999 |
| FR | 2 605 220 | 4/1988 |
| GB | 2 303 549 | 2/1997 |
| JP | 2005-507414 | 3/2005 |
| WO | WO 00/45777 | 8/2000 |
| WO | WO 01/06829 | 2/2001 |
| WO | WO 03/037830 | 5/2003 |

OTHER PUBLICATIONS

Huang et al., Journal of Biological Chemistry, 1982, 257(22), p. 13616.*
Baldwin et al. Biochem J. (1989) v. 261, pp. 197-204.
French Search Report for FR 02/05863, priority document for parent U.S. Appl. No. 10/436,050, Jan. 28, 2003, Examiner D. Klein.
Hashimoto, M. "Versatile Synthesis of Phenoxydiazirine-Based Fatty Acid Analogues and Photoreactive Galactosylceramide" Bioorganic and medicinal Chemistry Letters 12 (2002) 89-91.
Makoto Hashimoto et al., "Versatile Synthesis of Phenoxydiazirine-Based Fatty Acid Analogues and Photoreactive Galactosylceramide," Bioorganic & Medicinal Chemistry Letters, vol. 12, Issue 1, Jan. 7, 2002, pp. 89-91.
Zofall, M. "Two novel dATP analogs for DNA photoaffinity labeling" Nucleic Acids Research 28 (2000) 4382-90.
English language Derwent Abstract of DE 44 36 173, Sep. 5, 1996.
English language abstract of DE 197 26 184, Dec. 24, 1998.

* cited by examiner

*Primary Examiner*—Yong Chu
(74) *Attorney, Agent, or Firm*—Finnegan, Henderson, Farabow, Garrett & Dunner LLP

(57) ABSTRACT

Disclosed herein are a cosmetic composition comprising at least one diazirine active-agent compound comprising a diazirine covalently bonded to a cosmetic active agent, said at least one diazirine-active agent compound and the uses of the composition or of the compound, as well as cosmetic treatment processes using the composition or the compound.

12 Claims, No Drawings

PHOTOACTIVATABLE DIAZIRINE-ACTIVE AGENT COMPOUNDS, COMPOSITIONS COMPRISING THEM AND USES THEREOF

This is a divisional application of U.S. application Ser. No. 10/436,050, filed May 13, 2003, now U.S. Pat. No. 7,285,285 which claims the benefit of U.S. Provisional Application No. 60/386,571, filed Jun. 7, 2002, and which claims the benefit of priority under 35 U.S.C. § 119 to French Patent Application No. 02 05863, filed May 13, 2002, all of which are incorporated herein by reference.

Disclosed herein are cosmetic compositions comprising at least one photoactivatable compound, the uses of the photoactivatable compound, and compositions for fixing cosmetic active agents to a keratin material.

The products used for fixing cosmetic agents to keratin materials generally can have the drawback of being removed very quickly on washing or during other treatments.

Dyeing processes using photoactivatable compounds as dyes are known. For example, Patent Application No. FR 2 605 220 describes a process for dyeing keratin materials, which comprises placing the keratin materials in contact with an aromatic azide or an azidoindole and then exposing the keratin materials to a suitable light source to develop the color; Patent Application No. WO 01/06829 describes grafting of a photosensitive functional group of phenyl azide type onto a cosmetic active agent.

Processes are also known in which polymers or prepolymers are deposited on hair fibers in the presence of photoinitiators; and these fibers can then be irradiated. According to this process, U.S. Pat. No. 5,300,285 discloses, for example, silicones comprising vinyl groups; and Patent Application No. WO 00/45777 discloses prepolymers comprising a polyacrylate and/or polymethacrylate of a polyalkylenoxylated polyol.

In general, the known processes can have at least one of the following drawbacks:

the degree of grafting of the cosmetic active agent onto the keratin materials after irradiation can remain low: often the molar percentage of grafted cosmetic active agents relative to the amount of cosmetic active agents present in the solution used can be less than 10%, for example, certain products formed after irradiation, such as nitrenes, can rearrange to give compounds of ketenimine type which can react only with nucleophiles of amine type. Consequently, the degree of grafting of these compounds onto the keratin materials may be limited by the amount of nucleophiles of amine type present on the surface to be grafted, furthermore, the irradiation can be generally performed using wavelengths in the region of 254 nm, and this high-energy irradiation may have the consequence of degrading biological systems, for example, aromatic azide groups can be of low chemical stability, for example, in a reducing or oxidizing medium. Consequently, a treatment using compounds of this type may be relatively incompatible with permanent-waving or relaxing the hair.

The present inventors sought a composition that may afford long-lasting fixing of cosmetic active agents to a keratin material.

Disclosed herein are compounds that can, for example, in a single step, afford long-lasting fixing of a cosmetic active agent to a keratin material.

These compounds use diazirines. These compounds can provide the bonding between the cosmetic agent and the keratin materials: they can be fixed to the cosmetic agent and to the keratin materials by covalent grafting.

Diazirines are known as photochemical markers.

As used herein, the functional groups of diazirines can have the advantage of being able to be used to graft a cosmetic active agent to a keratin material without the need for photoinitiators.

With these diazirines, a higher degree of grafting can be obtained than that obtained by the processes according to the prior art; and this process can allow the use of wavelengths longer than 350 nm, which generally do not degrade proteins.

It has also been demonstrated that diazirine groups can have very good chemical stability, even in a reducing or oxidizing medium. In addition, the products such as carbenes that can form after irradiation, for example, irradiation performed using wavelengths ranging from 300 to 450 nm and further, for example, from 350 to 380 nm, can have the advantage of inserting rapidly into many types of bonds (C—H, C—C, C=C, N—H, O—H, S—H) which can, for example, be present in keratin materials or in chemical elements present at the surface of keratin materials.

Disclosed herein is a photoactivatable compound comprising a diazirine covalently bonded to a cosmetic active agent; this compound is referred to as a "diazirine-active agent compound".

The diazirine-active agent compound comprises a single photoactivatable group of the grafted diazirine type per active agent.

This compound can enable the covalent grafting of cosmetic active agents to keratin materials. For example, this grafting can take place in a single step.

In one embodiment, the diazirine disclosed herein is chosen from diazirines of formula (I):

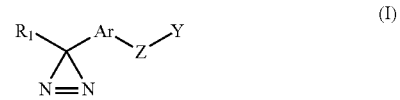

wherein:

—$R_1$ is chosen from a hydrogen atom, linear and branched $C_1$ to $C_{10}$ alkyl radicals, linear and branched $C_2$ to $C_{10}$ alkenyl radicals, linear and branched $C_2$ to $C_{10}$ alkynyl radicals, $CF_3$, $CCl_3$, $CBr_3$, $N(R')_3+$, $S(R')_2+$, $SH_2+$, $NH_3+$, $NO_2$, $SO_2R'$, C≡N, COOH, F, Cl, Br, I, OR', COOR', $SO_3H$, COR', SH, SR' and OH radicals, wherein R' is chosen from $C_1$ to $C_{10}$ alkyl radicals;

—Z is chosen from a single bond and a spacer group wherein the spacer group is a carbon-based chain chosen from linear, branched and cyclic, saturated and unsaturated $C_1$-$C_{100}$ carbon-based chains, for example, $C_1$-$C_{50}$ carbon-based chains, wherein said carbon-based chain may be interrupted with at least one hetero atom chosen from, for example, sulphur, oxygen, nitrogen, silicon, and phosphorus atoms and may also comprise at least one substituent chosen from, for example, hydroxyl, amine, thiol, carbamate, ether, acid, ester, amide, cyano and ureido groups;

For example, the spacer group can be chosen from polyols and polyalkylene glycols such as polyethylene glycol (PEG) and polypropylene glycol (PPG);

—Y is a functional group that can allow the covalent bond to be established between the functional group of the diazirine and the cosmetic active agent;

Y is a functional group chosen from alcohols; amines; thiols; thiosulphates; carboxylic acids and derivatives thereof such as anhydrides; acid chlorides; esters; acetals; hemiacetals; aminals; hemiaminals; ketones; aldehydes; α-hydroxy ketones; α-halo ketones; epoxides; lactones; thiolactones; azalactones; isocyanate; thiocyanate; imines; imides such as succinimides and glutimides; imido esters; aziridines; imidates; oxazine; oxazoline; oxazinium; oxazolinium; halogens such as fluorine, chlorine, iodine and bromine; chlorotriazines; chloropyrimidines; chloroquinoxalines; chlorobenzotriazoles; sulphonyl halides $SO_2X$, wherein X is chosen from F, Cl, I and Br; siloxanes; silanols; silanes; pyridyldithio derivatives; N-hydroxysuccinimide esters; activated vinyls and nonactivated vinyls including acrylonitriles; acrylic esters; methacrylic esters; crotonic acids; crotonic esters; cinnamic acids; cinnamic esters; styrenes; butadienes; vinyl ethers; vinyl ketones; maleic esters; maleimides; vinyl sulphones; hydrazines; and phenyl glyoxal; and —Ar is an aromatic nucleus chosen from the following groups:

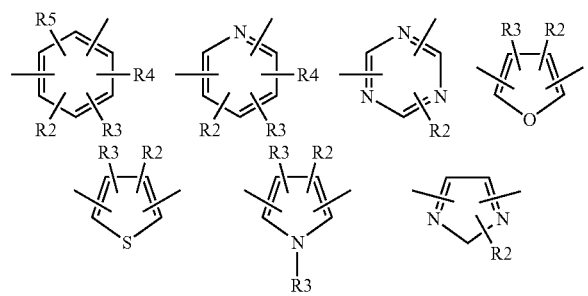

wherein:

—$R_2$, $R_3$, $R_4$ and $R_5$, which may be identical or different, are each chosen from a hydrogen atom, linear and branched $C_1$ to $C_{10}$ alkyl radicals, linear and branched $C_2$ to $C_{10}$ alkenyl radicals, linear and branched $C_2$ to $C_{10}$ alkynyl radicals, $CF_3$, $CCl_3$, $CBr_3$, $N(R')_3+$, $S(R')_2+$, $SH_2+$, $NH_3+$, $NO_2$, $SO_2R'$, C≡N, COOH, F, Cl, Br, I, OR', COOR', COR', SH, SR', OH, and $SO_3H$ radicals, wherein R' is chosen from $C_1$ to $C_{10}$ alkyl radicals.

The diazirine-active agent compound may, for example, be synthesized by forming a covalent bond between a diazirine, for example, the group Y of a diazirine chosen from diazirines of formula (I), and a functional group of the cosmetic active agent capable of forming a covalent bond with the diazirine. This bond can be established by performing standard chemical reactions. If need be, the formation of the bond may be preceded by a reaction aimed at protecting another site of the cosmetic active agent that it is not desired to have react. The standard chemical reactions for protection and deprotection of reactive groups can then performed.

Also disclosed herein is a cosmetic composition comprising, in at least one cosmetically acceptable solvent, at least one diazirine-active agent compound. For example, the at least one diazirine-active agent compound can comprise a diazirine chosen from diazirines of formula (I).

The cosmetic compositions disclosed herein can comprise, for example, at least one cosmetically acceptable solvent chosen, for example, from water and ethanol. The at least one cosmetically acceptable solvent may further, for example, be chosen from organic solvents such as $C_5$ to $C_{10}$ alkanes, acetone, methyl ethyl ketone, methyl acetate, ethyl acetate, butyl acetate, dimethoxyethane and diethoxyethane.

In one embodiment, the cosmetic active agent used herein may comprise at least one group capable of giving covalent reactions with the group Y of the diazirine chosen from diazirines of formula (I). Such cosmetic active agents may, for example, be chosen from natural soluble polymers, synthetic soluble polymers, natural insoluble polymers, synthetic insoluble polymers, mineral particles, such as mineral metallic particles and mineral non-metallic particles, organic particles such as latices, polystyrenes, and silicones, pigments, sunscreens, antioxidants, and dyes.

As used herein, the expression "soluble or insoluble polymers" means water-soluble or water-insoluble polymers.

The cosmetic active agents in polymer form may, for example, be chosen from silicones, cationic polymers and amphoteric polymers.

The cosmetic active agents in the form of mineral particles may, for example, be chosen from nacres, pigments, nanopigments (mean size of the primary particles can range, for example, from 5 nm to 100 nm, further, for example, from 10 nm and 50 nm) of coated and uncoated metal oxides, for example, nanopigments of titanium oxide (amorphous and crystallized in rutile and anatase form), of iron oxide, of zinc oxide, of zirconium oxide, and of cerium oxide. The cosmetic active agents in the form of mineral particles may also, for example, be chosen from alumina and aluminum stearate.

The cosmetic active agents in the form of sunscreens may, for example, be chosen from 1,3,5-triazine derivatives, dibenzoylmethane derivatives, cinnamic derivatives, anthranilates; salicylic derivatives, camphor derivatives; benzophenone derivatives; β,β-diphenylacrylate derivatives, benzotriazole derivatives; benzalmalonate derivatives; benzimidazole derivatives; imidazolines; the bis(benzazolyl) derivatives as described in Patent Nos. EP 669 323 and U.S. Pat. No. 2,463,264; p-aminobenzoic acid (PABA) derivatives; the methylenebis(hydroxyphenyl)benzotriazole derivatives as described in patent application Nos. U.S. Pat. No. 5,237,071, U.S. Pat. No. 5,166,355, GB 2 303 549, DE 197 26 184 and EP 893 119; screening polymers and screening silicones such as those described, for example, in Patent Application No. WO-93/04665; and dimers derived from α-alkylstyrene such as those described in Patent Application DE No. 198 55 649, 4,4-diarylbutadienes such as those described in Patent Application Nos. EP 0 967 200 and DE 197 55 649.

The cosmetic active agents in the form of dyes can be chosen, for example, from nitrobenzene dyes, aromatic dyes, aminobenzene dyes, azo dyes, anthraquinone dyes, aromatic diamines, aminophenols, phenols, naphthols, porphyrines, tetraphenylporphyrines, metalloporphyrines, phthalocyanins, carotenoids, flavonoids, and fluorescent molecules such as fluorescein, rhodamine and coumarin.

The cosmetic compositions disclosed herein may comprise at least one diazirine-active agent compound, wherein the at least one diazirine-active agent compound comprises a diazirine covalently bonded to a cosmetic active agent.

The cosmetic composition may comprise, for example, from 0.001% to 90%, by weight, further, for example, from 0.01% to 50% by weight, and even further, for example, from 0.1% to 10% by weight of the at least one diazirine-active agent compound, relative to the total weight of the composition.

The compositions disclosed herein may also comprise at least one other cosmetic agent or constituent that is not bonded to the diazirine.

The at least one other cosmetic agent may be chosen, for example, from polymers, mineral particles, organic particles, sunscreens, fatty substances, softeners, antioxidants, free-radical scavengers, emollients, α-hydroxy acids, moisturizers, vitamins, insect repellents, fragrances, anti-inflammatory agents, substance P antagonists, fillers and dyes.

When the compositions disclosed herein comprise at least one other cosmetic agent, said at least one other cosmetic agent may be present in an amount ranging, for example, from 0.01% to 70% by weight, further, for example, from 0.1% to 50% by weight, relative to the total weight of the composition.

These compositions may also comprise at least one activator for the photoactivatable compounds, for example, polyamines.

The cosmetic composition disclosed herein may be used, for example, as a coloring agent for the skin, the nails and/or the hair, as a moisturizer, as an agent for increasing the sheen, for example, of the hair (sheen agent), as a sunscreen, as a conditioner and/or as an agent for shaping keratin fibers.

The cosmetic compositions disclosed herein may, for example, be introduced into any existing hair treatment formulations, for example, into shampoos.

As used herein, the keratin material means head hair, eyelashes, eyebrows, other hairs, nails or skin.

Also disclosed herein is the use of at least one diazirine-active agent compound, for example, in a cosmetic treatment process. Such a process is a cosmetic process for treating a keratin material, for example, human keratin material such as hair, to modify at least one of the properties of the keratin material.

Also disclosed herein is a cosmetic treatment process comprising applying to a keratin material at least one diazirine-active agent compound disclosed herein and exposing the keratin material to radiation of at least one wavelength ranging, for example, from 300 to 450 nm, further, for example, from 350 to 400 nm and even further, for example, from 350 to 380 nm.

Even further disclosed herein is the use of the cosmetic composition disclosed herein in a cosmetic treatment process, for example, as a coloring agent, as a moisturizer, as an agent for increasing the sheen, for example, of the hair (sheen agent), as a sunscreen, as a conditioner and/or as an agent for shaping keratin fibers.

Also disclosed herein is a cosmetic treatment process comprising applying to a keratin material the cosmetic composition disclosed herein and exposing the keratin material to radiation of at least one wavelength ranging, for example, from 300 to 450 nm, further, for example, ranging from 350 to 400 nm and even further, for example, ranging from 350 to 380 nm. This process may be performed, for example, in at least one step.

Also disclosed herein is the use of at least one diazirine, for example, at least one diazirine chosen from diazirines of formula (I), in a cosmetic treatment. For example, this cosmetic treatment can be directed towards modifying the chemical reactivity of the keratin material, for example, the hair.

Also disclosed herein is a process comprising applying to a keratin material a composition comprising at least one diazirine chosen from diazirines of formula (I), optionally in the presence of at least one cosmetic active agent, and exposing said keratin material to radiation of at least one wavelength ranging, for example, from 300 to 450 nm, further, for example, ranging from 350 to 380 nm.

This process, which can use the at least one diazirine to graft simple groups onto a surface, can make it possible to modify the chemical reactivity of this surface and thus to prepare it for a subsequent treatment. In the case of the hair, this technique may be used to specifically modify certain areas of the head of hair, for example, if this technique is combined with a dyeing treatment, certain locks of a head of hair may be specifically dyed.

Also disclosed herein is a process comprising applying to a keratin material sequentially and in any order a cosmetic composition comprising at least one diazirine chosen from diazirines of formula (I) and a composition comprising at least one cosmetic active agent, and exposing said keratin material to radiation of at least one wavelength ranging, for example, from 300 to 450 nm and further, for example, from 350 to 380 nm.

In one embodiment, after placing the composition(s) in contact with the keratin material, the excess composition can be removed.

The processes disclosed herein may also be performed after at least one preliminary treatment of the keratin material. This at least one preliminary treatment can be chosen from treatments using a reducing composition, permanent-waving, dyeing using oxidation dyes, bleaching, shampooing and styling treatments.

The examples that follow illustrate embodiments disclosed herein without limiting its scope.

EXAMPLES

Example 1

Synthesis of a Diazirine-active Agent Compound

The active agent used was a poly(ethylene oxide/propylene oxide).

The synthesis was performed starting with a diazirine chosen from diazirines of formula (I), wherein $R_1$ is a trifluoromethyl group, Ar is a phenyl group, Z is a bond and Y is the N-hydroxysuccinimide ester of a carboxylic acid group, i.e., diazirine compound D as shown below.

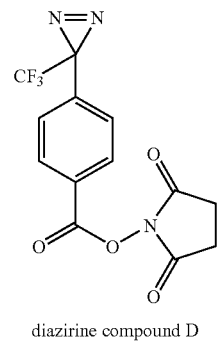

diazirine compound D

The active agent used was a copolymer of ethylene oxide and of propylene oxide bearing an amine end functional group, Jeffamine M-1000 sold by Texaco.

To perform this synthesis, an aqueous solution at a concentration of 20% by mass of Jeffamine M-1000 was placed under stirring.

The pH was adjusted to 8.5 with the required amount of hydrochloric acid or of sodium hydroxide.

A solution of 2 g of diazirine compound D in 10 ml of DMF was prepared. This solution was added slowly to the Jeffamine solution and was stirred at room temperature for 7 hours.

The solution was then dialysed for 12 hours in distilled water.

A ready-to-use aqueous solution of diazirine-active agent compound, PEO/PPO/diazirine, with a content ranging from 15% to 20% by weight, was thus obtained.

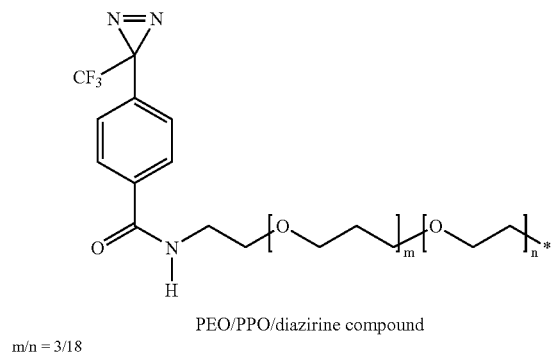

PEO/PPO/diazirine compound
m/n = 3/18

Example 2

Hair Treatment with a Diazirine-active Agent Compound

The solution of diazirine-active agent compound, PEO/PPO/diazirine, was applied to locks of natural hair, at a quantity of 0.5 ml of solution per lock.

The locks were dried using a hair drier until the water had evaporated.

The locks were then irradiated at 360 nm for 30 minutes.

Example 3

Hair Treatment with a Diazirine Compound

A 1% solution of diazirine compound D in isododecane was applied to hair.

The isododecane was allowed to evaporate, optionally by drying the locks with a hair drier, and the locks were then irradiated at 360 nm for 30 minutes.

What is claimed is:

1. A cosmetic composition comprising,
at least one cosmetically acceptable solvent, and
at least one photoactivatable diazirine-active agent compound which comprises a diazirine covalently bonded to a cosmetic active agent, wherein the cosmetic agent is chosen from natural soluble polymers, synthetic soluble polymers, natural insoluble polymers, synthetic insoluble polymers, sunscreens, mineral particles, organic particles, antioxidants, and dyes, and
wherein the diazirine is chosen from diazirines of formula (I):

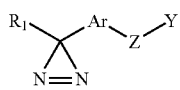 (I)

wherein:
— $R_1$ is chosen from a hydrogen atom, linear and branched $C_1$ to $C_{10}$ alkyl radicals, linear and branched $C_2$ to $C_{10}$ alkenyl radicals, linear and branched $C_2$ to $C_{10}$ alkynyl radicals, $CF_3$, $CCl_3$, $CBr_3$, $N(R')_3+$, $S(R')_2+$, $SH_2+$, $NH_3+$, $NO_2$, $SO_2R'$, $C\equiv N$, COOH, F, Cl, Br, I, OR', COOR', $SO_3H$, COR', SH, SR' and OH radicals, wherein R' is chosen from $C_1$ to $C_{10}$ alkyl radicals;

— Z is chosen from a single bond and a spacer group, wherein the spacer group is a carbon-based chain chosen from linear, branched and cyclic, saturated $C_1$-$C_{100}$ carbon-based chains, wherein said carbon-based chain may be interrupted with at least one hetero atom and may also comprise at least one substituent;
— Y is an aldehyde, and
— Ar is an aromatic nucleus:

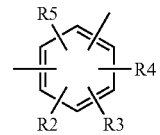

wherein:
— $R_2$, $R_3$, $R_4$ and $R_5$, which may be identical or different, are each chosen from a hydrogen atom, linear and branched $C_1$ to $C_{10}$ alkyl radicals, linear and branched $C_2$ to $C_{10}$ alkenyl radicals, linear and branched $C_2$ to $C_{10}$ alkynyl radicals, $CF_3$, $CCl_3$, $CBr_3$, $N(R')_3+$, $S(R')_2+$, $SH_2+$, $NH_3+$, $NO_2$, $SO_2R'$, $C\equiv N$, COOH, F, Cl, Br, I, OR', COOR', COR', SH, SR', OH and $SO_3H$ radicals, wherein R' is chosen from $C_1$ to $C_{10}$ alkyl radicals.

2. The cosmetic composition according to claim 1, wherein, in the definition of Z, the spacer group is a carbon-based chain chosen from linear, branched and cyclic, saturated $C_1$-$C_{50}$ carbon-based chains.

3. The cosmetic composition according to claim 1, wherein, in the definition of Z, the at least one hetero atom is chosen from sulphur, oxygen, nitrogen, silicon, and phosphorus atoms.

4. The cosmetic composition according to claim 1, wherein, in the definition of Z, the at least one substituent is chosen from hydroxl, amine, thiol, carbamate, ether, acid, ester, amide, cyano, and ureido groups.

5. The cosmetic composition according to claim 1, wherein, in the definition of Z, the spacer group is chosen from polyols and polyalkylene glycols.

6. The cosmetic composition according to claim 5, wherein the spacer group is chosen from polyethylene glycol and polypropylene glycol.

7. The cosmetic composition according to claim 1, wherein the cosmetic active agent is a dye chosen from nitrobenzene dyes, aromatic dyes, aminobenzene dyes, azo dyes, anthraquinone dyes, aromatic diamines, aminophenols, phenols, naphthols, porphyrines, tetraphenylporphyrines, metalloporphyrines, phthalocyanins, carotenoids, flavonoids, and fluorescent molecules.

8. The cosmetic composition according to claim 1, wherein the at least one diazirine-active agent compound is present in an amount ranging from 0.001% to 90% by weight, relative to the total weight of the composition.

9. The cosmetic composition according to claim 8, wherein the at least one diazirine-active agent compound is present in an amount ranging from 0.01% to 50% by weight, relative to the total weight of the composition.

10. The cosmetic composition according to claim 9, wherein the at least one diazirine-active agent compound is present in an amount ranging from 0.1% to 10% by weight, relative to the total weight of the composition.

11. The cosmetic composition according to claim 1, further comprising at least one other cosmetic agent that is not bonded to the diazirine chosen from polymers, mineral particles, organic particles, sunscreens, dyes, fatty substances, softeners, antioxidants, free-radical scavengers, emollients, α-hydroxy acids, moisturizers, vitamins, insect repellents, fragrances, anti-inflammatory agents, substance P antagonists, and fillers.

12. The cosmetic composition according to claim 1, further comprising at least one activator, wherein the at least one activator is chosen from polyamines.

* * * * *